(12) United States Patent
Sonkusale et al.

(10) Patent No.: US 11,121,334 B2
(45) Date of Patent: Sep. 14, 2021

(54) 3D GRAPHENE TRANSISTOR

(71) Applicant: Trustees of Tufts College, Medford, MA (US)

(72) Inventors: Sameer Sonkusale, Arlington, MA (US); Shideh Kabiri Ameri Abootorabi, Medford, MA (US); Pramod Kumar Singh, Ambedkar Nagar (IN)

(73) Assignee: Trustees of Tufts College, Medford, MA (US)

( * ) Notice: Subject to any disclaimer, the term of this patent is extended or adjusted under 35 U.S.C. 154(b) by 590 days.

(21) Appl. No.: 15/321,296

(22) PCT Filed: Jun. 26, 2015

(86) PCT No.: PCT/US2015/037897
§ 371 (c)(1),
(2) Date: Dec. 22, 2016

(87) PCT Pub. No.: WO2015/200758
PCT Pub. Date: Dec. 30, 2015

(65) Prior Publication Data
US 2017/0200909 A1    Jul. 13, 2017

Related U.S. Application Data

(60) Provisional application No. 62/017,458, filed on Jun. 26, 2014.

(51) Int. Cl.
*H01L 51/05* (2006.01)
*G01N 27/414* (2006.01)
(Continued)

(52) U.S. Cl.
CPC ........ *H01L 51/0558* (2013.01); *A61B 5/1473* (2013.01); *A61B 5/14528* (2013.01);
(Continued)

(58) Field of Classification Search
CPC ............. H01L 51/0558; H01L 29/1606; H01L 51/0045; H01L 29/778; H01L 29/0665;
(Continued)

(56) References Cited

U.S. PATENT DOCUMENTS 6,969,539 B2 * 11/2005 Gordon .................. C07F 9/091
427/255.29
8,703,523 B1 * 4/2014 Biener ................ H01L 29/0673
438/82

(Continued)

FOREIGN PATENT DOCUMENTS

WO         2009/029984        3/2009
WO       WO2009029984    *   3/2009
(Continued)

*Primary Examiner* — Benjamin Tzu-Hung Liu
(74) *Attorney, Agent, or Firm* — Occhiuti & Rohlicek LLP

(57) ABSTRACT

A field effect transistor having a channel that comprises three-dimensional graphene foam. The subject matter of the invention concerns a three dimensional field-effect transistor having a channel based on graphene foam and the use of ionic liquid as a gate. The graphene foam is made of a three-dimensional network of single and double layer graphene that extends in all the three dimensions. Metal contacts on either end of the graphene foam form the drain and source contacts of the transistor.

18 Claims, 7 Drawing Sheets

(51) Int. Cl.
| | |
|---|---|
| *H01L 29/16* | (2006.01) |
| *H01L 51/00* | (2006.01) |
| *H01L 29/778* | (2006.01) |
| *H01G 9/20* | (2006.01) |
| *H01L 29/06* | (2006.01) |
| *A61B 5/145* | (2006.01) |
| *A61B 5/1473* | (2006.01) |

(52) U.S. Cl.
CPC ..... *G01N 27/4146* (2013.01); *H01L 29/1606* (2013.01); *H01L 51/0045* (2013.01); *G01N 27/4145* (2013.01); *H01G 9/2013* (2013.01); *H01L 29/0665* (2013.01); *H01L 29/778* (2013.01)

(58) Field of Classification Search
CPC ............ G01N 27/4146; G01N 27/4145; A61B 5/14528; A61B 5/1473; H01G 9/2013

See application file for complete search history.

(56) References Cited

U.S. PATENT DOCUMENTS

| | | | |
|---|---|---|---|
| 9,293,536 B2* | 3/2016 | Nourbakhsh | H01L 29/42384 |
| 9,852,824 B2* | 12/2017 | Worsley | H01B 1/08 |
| 2010/0320437 A1* | 12/2010 | Gordon | B82Y 10/00 |
| | | | 257/9 |
| 2013/0037780 A1* | 2/2013 | Kivioja | G01L 1/2293 |
| | | | 257/26 |
| 2013/0285970 A1* | 10/2013 | Ahn | G06F 3/044 |
| | | | 345/173 |
| 2014/0070170 A1* | 3/2014 | Andersson | G01N 27/4146 |
| | | | 257/29 |
| 2014/0074253 A1* | 3/2014 | Lieber | A61L 27/025 |
| | | | 623/23.72 |
| 2016/0005894 A1* | 1/2016 | Zhang | H01L 31/1804 |
| | | | 257/29 |
| 2016/0051735 A1* | 2/2016 | Slepian | A61N 1/326 |
| | | | 600/301 |

FOREIGN PATENT DOCUMENTS

| | | |
|---|---|---|
| WO | 2012/112746 | 8/2012 |
| WO | WO2012112746 * | 8/2012 |

* cited by examiner

3D GRAPHENE TRANSISTOR

CROSS REFERENCE TO RELATED APPLICATIONS

This application is the National Stage under 35 USC 371 of PCT/US2015/037897, filed on Jun. 26, 2015, which claims the benefit of the priority date of U.S. Provisional Application No. 62/017,458, filed Jun. 26, 2014. The contents of the aforementioned application is incorporated herein in its entirety.

STATEMENT OF FEDERAL FUNDING

This invention was made with government support under grant 0955024 awarded by the National Science Foundation. The government has certain rights in the invention.

FIELD OF DISCLOSURE

The disclosure relates to transistors, and in particular, to FETS.

BACKGROUND

In many cases, intimate contact with the environment is a good way to sense some physical parameter. For example, to test pH, one places litmus paper in direct physical contact with the liquid under test so that a reaction can occur. To measure temperature, typically some object is placed in contact with the environment so that a temperature-induced expansion can take place in that object.

A FET sealed in a package cannot carry out such sensing. Moreover, even if it could be placed in contact with the environment, the conventional FET's planar structure limits the amount of surface area that can be exposed to the environment. In addition, a conventional FET is a static structure. It cannot deform. This limits its applications.

A further difficulty arises from the fact that a FET often has regions that have been doped with highly toxic substances. These structures are thus not commonly regarded as particularly biocompatible.

SUMMARY

The subject matter of the invention concerns a three dimensional field-effect transistor having a channel based on graphene foam and the use of ionic liquid as a gate. The graphene foam is made of a three-dimensional network of single and double layer graphene that extends in all the three dimensions. Metal contacts on either end of the graphene foam form the drain and source contacts of the transistor.

Making a solid-state gate for a complex three dimensional structure is challenging. In the invention, this difficulty is avoided by using a liquid gate in the three-dimensional graphene channel. Such a gate is formed by an ionic liquid electrolyte.

Liquid gating provides a natural all-around electrostatic control of the transistor channel. Ionic liquids are non-volatile, highly polar, highly conductive, high ionic strength, room-temperature electrolytes that are ideally suited for use as a gate dielectric where they can cause huge carrier accumulation in semiconductor material controllable by electric field. This is possible due to the formation of electrical double layers (EDLs) on the surface of semiconductor. As a result of having large concentration of holes (electrons) in the semiconductor and anions (cations) in the electrolyte, such double layers have a huge capacitance per unit surface area. The resulting higher value of gate capacitance results in higher carrier concentration, higher on-state current and lower operating voltages.

The invention thus provides a three dimensional field-effect transistor based on graphene foam immersed in ionic liquid. In this transistor, the channel is composed of a complex three dimensional network of free standing single to double layer graphene bathed in an ionic liquid gate.

In another aspect, the invention features a three-dimensional field-effect transistor comprising a complex three-dimensional network of single to double layer graphene foam that functions as a channel and that is immersed in an ionic liquid. The electrolytic double layer capacitance at the interface between the ionic liquid and the graphene provides all-around three-dimensional liquid gating of the transistor. The high surface area of the graphene foam results in a high aspect ratio that provides a higher current carrying capacity than a two-dimensional graphene transistor. Moreover, the nanometer wide electrolytic double layer formed at the high surface area interface between the ionic liquid and the graphene results in a large gate capacitance that, in turn, facilitates low voltage operation. As a result of its all-carbonaceous form and liquid gating, a transistor according to the invention is particularly suited as an electronic interface with biological structures for applying electrical stimuli or recording of biopotentials and ion channel currents.

In some embodiments, the transistor is sensitive to the pH, or equivalently, pOH, of the local gate environment. The pH dependent field effect enables the transistor to be used in a highly sensitive pH sensing device that is also biocompatible.

The transistor can also be used in detection of dissolved gases and chemicals. It can also be chemically functionalised with atpamers, antibodies, molecularly imprinted polymers, fluorescent markers or other labels of protein detection, RNA, DNA, metabolites, hormones, etc. As a result, the transistor can be used as a chemical or biological sensor.

In addition, the properties of the transistor change as a result of strain. These properties that change include more than merely resistance. For example, drain current can change as a function of strain, with a sensitivy of 0.374 mA per percentage point of strain being achievable.

This dependence provides an ability to measure mechanical strain, force, or pressure. As a result, the transistor according to the invention is useful as a mechanical transducer. The use of a stretchable graphene foam in a strain sensor is particularly useful because such a foam is inherently tolerant to defects. This tolerance is believed to arise at least in part from the random network topology in a foam, which provides a carrier pathway even at high strain when local defects could manifest themselves within the device.

Additionally, the use of a transistor as a sensor provides the opportunity of intrinsic amplification of the strain response.

The transistor is thus a multi-modal device that is sensitive to electric fields, which arise in connection with the existence of voltage and/or current, mechanical movement, which arises in the presence of stress, strain, or pressure force, and to chemical and biological targets. This enables the transistor to be used in connection with measuring multiple inputs at the same time. For example, such a transistor can be used to measure both biopotential and mechanical movement. This is particularly useful in the study of cardiac tissue and cells. The transistor can also be used to measure both chemical and electrical signals at the same time, which makes it useful in the study of neuronal activity. The transistor can also be used to harvest both chemical and mechanical information at the same time, which is useful in the study of cancer cells and in the microenvironment of stem cells.

Also included within the scope of the invention is a method for making the three-dimensional graphene foam, the transistor itself and any device that incorporates it, and the use of liquid gating in a transistor. Also included are different implementations of the transistor, either on hard or soft substrates. These substrates can include, but are not limited to, glass, polyimide, PET, or organic polymers such as PDMS, parylene, hydrogel, or paper. Also within the scope of the invention is a device that uses the transistor in a three-dimensional biological scaffold. Also within the scope of the invention is a device that incorporates the transistor as a sensor of chemical and bilogical processes, with and without functionalization. Also within the scope of the invention is a device that uses the transistor as a mechanical sensor for sensing stress, strain, pressure, force, or any movement. Also within the scope of the invention is a device that incorporates the transistor for multimodal sensing in which multiple measurements of different modes are made at the same time. These include measurements of any two mechanical, chemical, biological, or electronic parameters in any combination.

Applications of the transistor include its use in the next generation of electronic devices beyond CMOS technology, its use as a sensor in tissue or cellular microenvironments, for example as part of a cardiac or neuronal implant, or as a chemical and biological sensor for general health-related parameters or environmental parameters.

In one aspect, the invention features an apparatus comprising a field effect transistor having a channel that comprises three-dimensional graphene foam.

In some embodiments, the apparatus further includes an ionic liquid that bathes the foam. Among these are embodiments in which the ionic liquid comprises 1-Butyl-3-methylimidazolium hexafluorophosphate.

Embodiments include those in which the foam comprises bilayer graphene, monolayer graphene, or both.

In some embodiments, the graphene is coated with a hydrophilic agent. Among these are embodiments in which the agent comprises $HfO_2$.

Embodiments include those in which the apparatus includes a sensor, with the transistor being incorporated in the sensor. Among these are embodiments in which a change in a transistor property forms a basis for sensor measurement. Sensors include biological sensors, including those for in vivo measurements, chemical sensors, strain sensors, and pH sensors.

In some embodiments, the apparatus includes a tissue scaffold that incorporates the transistor therein.

These and other features of the invention will be apparent from the following detailed description and the accompanying remarks, in which:

DETAILED DESCRIPTION

Figure 1:
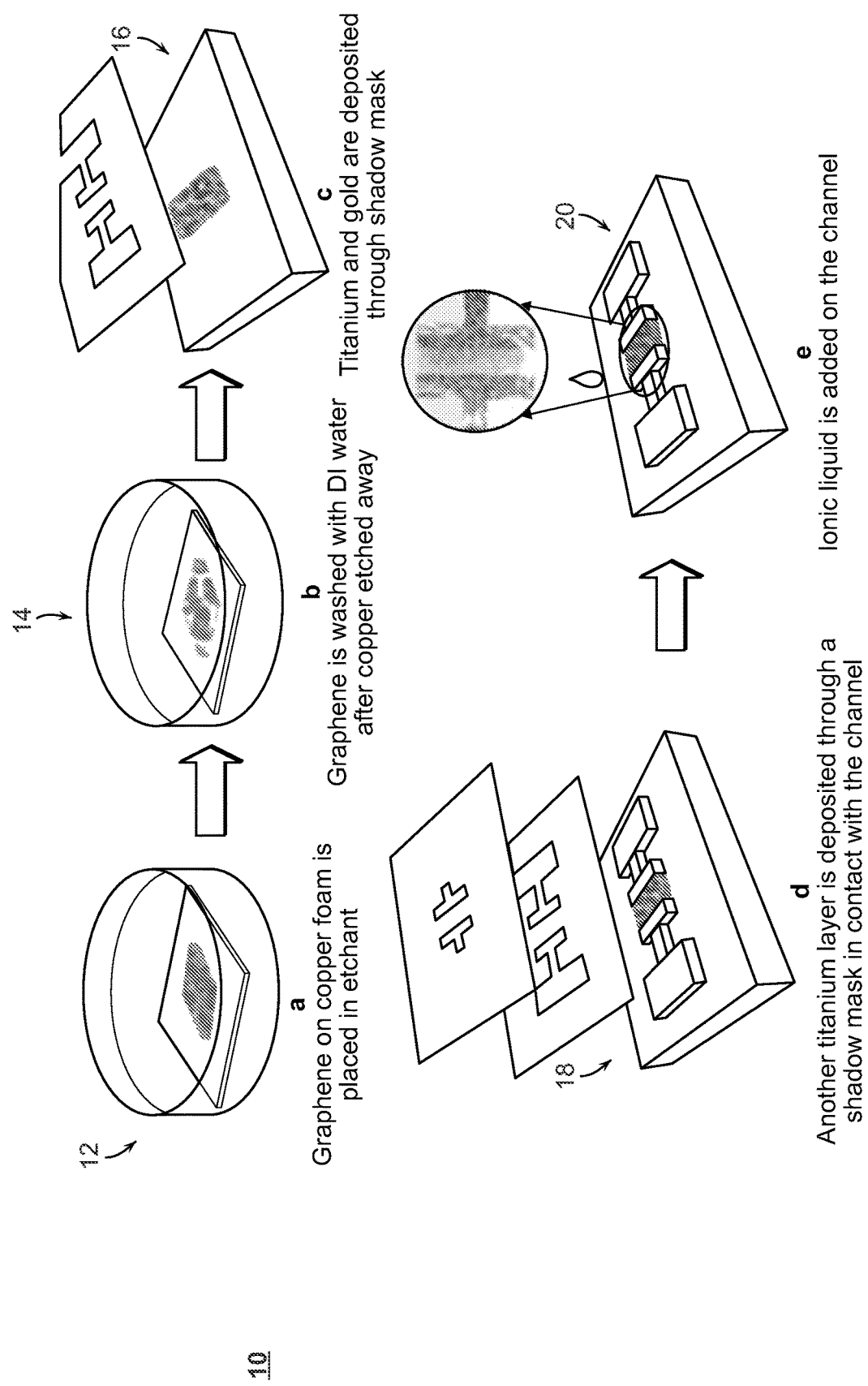
FIG. 1 illustrates steps in a device fabrication process.
Figure 2:
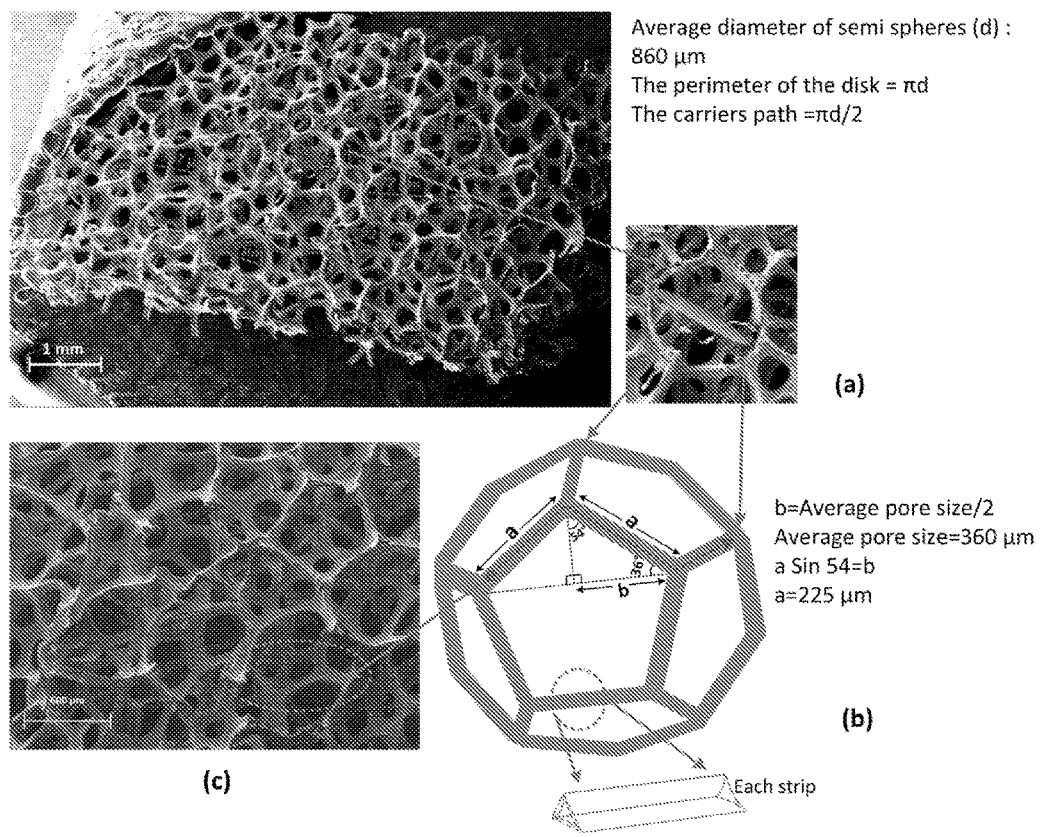
FIG. 2 shows a structural model of a foam together with estimated electron pass lengths.
Figure 3:
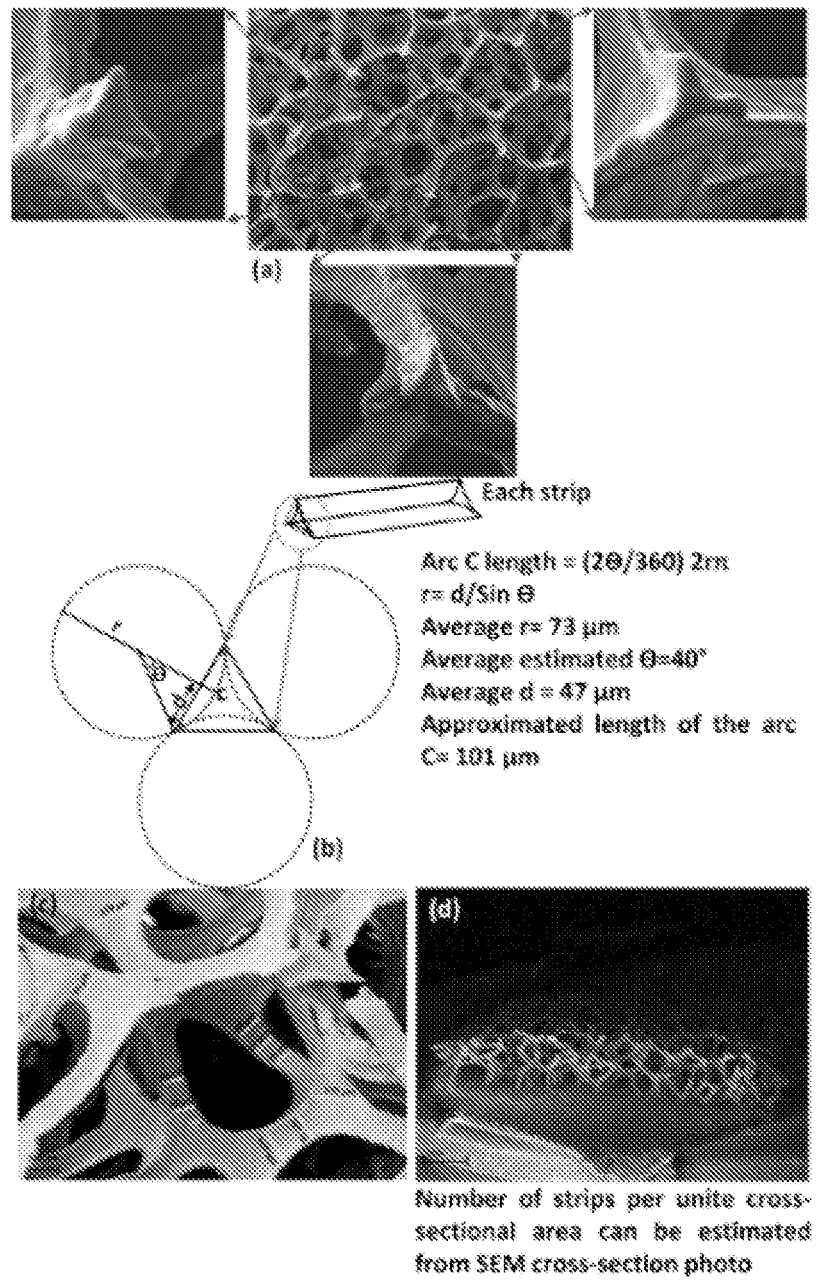
FIG. 3 shows a structural model of a foam and an estimate of an effective width of a transistor.

FIG. 1 shows the fabrication process flow 10. The process begins by using CVD to grow graphene on the copper foam (step 12). The CVD grown monolayer graphene on the copper foil is then held in copper etchant to etch away copper (step 14). A useful etchant is a 0.06 molar solution of ferric chloride, $FeCl_3$. The graphene is then transferred onto a glass substrate and rinsed with deionized water to clean any chemical residues left on the surface of the graphene as a result of the etching process. Preferably, the glass substrate is first cleaned using the RCA method (hydrogen peroxide, 30%, ammonium hydroxide, 27%, and deionized water with the 1:1:5 proportions respectively at 80° C. for 10 min).

Figure 5:
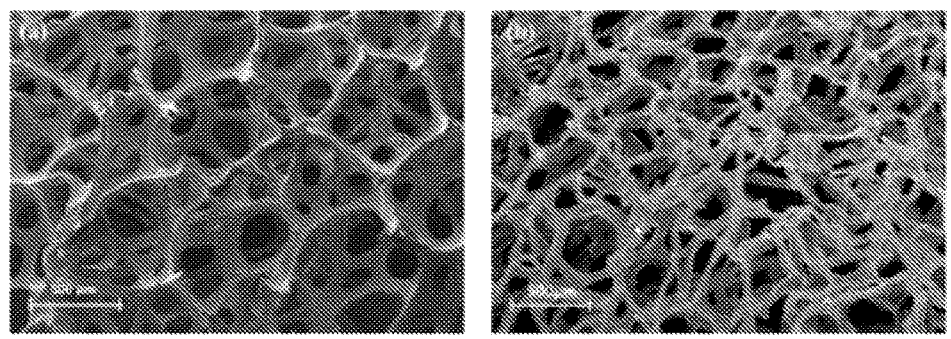
FIG. 5 shows SEM images of graphene foam before and after etching.

The left side of FIG. 5 shows an SEM image of graphene foam before this etching step. The right side of FIG. 5 shows a similar image after the etching step. It is apparent from comparison of these figures that the foam is an interconnected network of single to double layer graphene strips and that this three-dimensional structure survives etching.

The next step is to form drain and source contacts (step 16). This is carried out by deposition through a shadow mask using electron beam evaporation. In one embodiment, the titanium is deposited to a thickness of 10 nm followed by deposition of a 50 nm gold layer. In another embodiment, the titanium layer is 20 nm and the gold layer is 220 nm.

In another deposition step (step 18), 10 nm of titanium is deposited through another shadow mask to cover the gold on the source and drain where contact is made with the channel. This forms a protective layer against ion leakage.

Optionally, the contacts are covered with epoxy to prevent contact between the solution and the electrodes.

Finally, the shadow mask is removed and ionic liquid is added to the channel (step 20). A metal electrode is suspended in the ionic liquid to apply a gate voltage. In one embodiment, the ionic liquid is 1-Butyl-3-methylimidazolium hexafluorophosphate ($BmimPF_6$, 98%). In one embodiment, the device is about 600 microns long and 5 mm wide.

In one embodiment that is suited for use as a pH meter, the graphene is coated with 20 nm of $HfO_2$ using ALD. This is because the sensing mechanism for a graphene FET is based on absorbing chemical and biological molecules on the surface. Since graphene is inherently hydrophobic, adding a layer of $HfO_2$ creates a hydrophylic surface and increases the pH sensitivity of the resulting sensor. In this embodiment, a solution with a pH between 3 and 10 is prepared by adding NaOH and HCL to a phosphate buffered saline (PBS). This serves as the gate with an Ag/AgCl reference electrode used to apply a gate voltage bias.

The resulting device is ideal as a scaffold with inherent pH responsivity for tissue engineering applications. Such a device is more sensitive than known pH meters. This superior sensitivity is believed to arise from the unique three-dimensional structure of the device, which provides a higher surface area and therefore a greater pH-dependent field effect of transistor behavior. This greater sensitivity is improved further by the use of the hafnium oxide layer, which provides a hydrophilic surface that improves interaction with an aqueous based ionic liquid in the channel.

Figure 4:
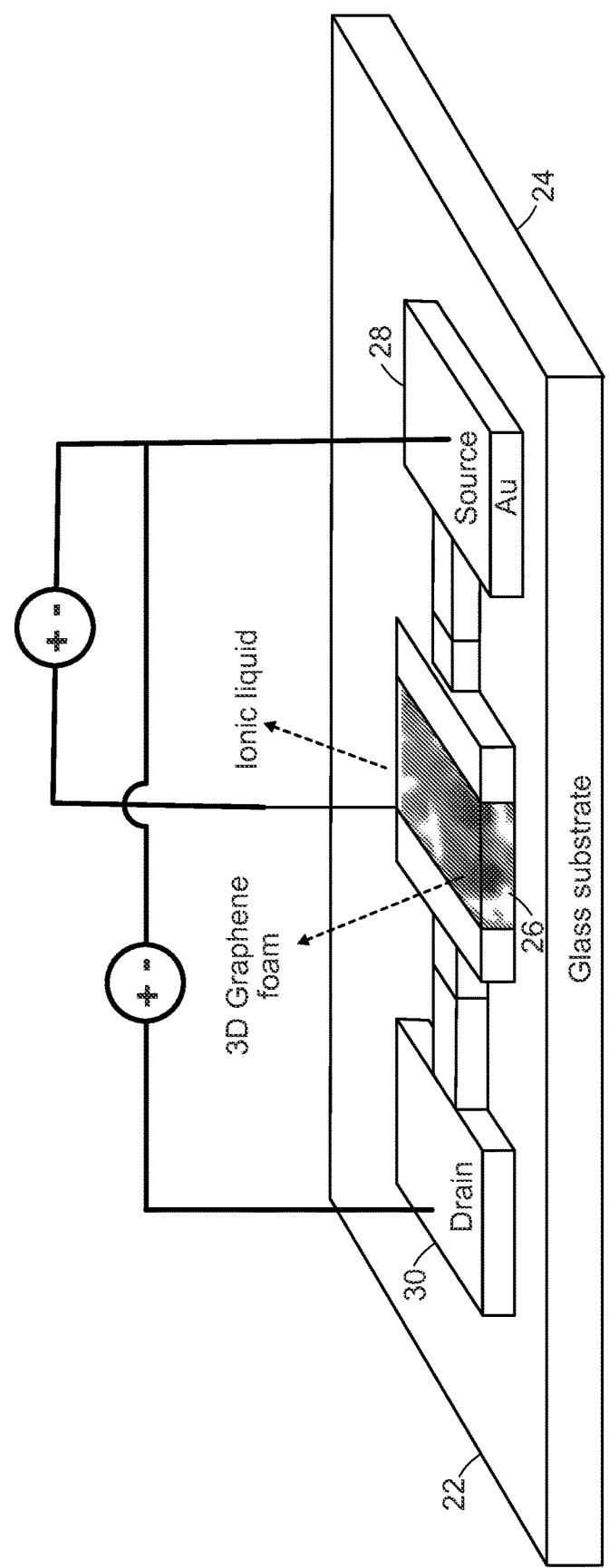
FIG. 4 is a schematic of a liquid gated graphene transistor.

FIG. 4 shows a schematic illustration of the graphene-based transistor 22 formed on a substrate 24. The three dimensional graphene foam serves as the active channel layer 26 with an ionic liquid serving as the gate of the transistor. In one embodiment, the ionic liquid is 1-Butyl- 3-methylimidazolium hexafluorophosphate, Bmim PF$_6$, 98%. The transistor 22 further includes metal contacts for a source terminal 28 and a drain terminal 30.

The graphene layers in the foam are naturally suspended above the substrate 24. This suppresses undesirable substrate effects that plague conventional two-dimensional graphene transistors, thus achieving high carrier mobility. For example, in a planar two-dimensional graphene transistors realized on a substrate, overall mobility of the charge carriers is diminished because of extrinsic scattering from phonons due to trapped charges at the graphene-dielectric interface. Mobility of high quality graphene ranges between $10^3$ cm$^2$V$^{-1}$s$^{-1}$ for graphene grown on silicon. But for suspended graphene, this mobility rises to $10^6$ cm$^2$V$^{-1}$s$^{-1}$. Moreover, using ionic liquid as a gate results in a large capacitance at the liquid-channel interface allowing for low voltage operation of the device.

In one embodiment, the transistor has a gate length of 600 μm and width of 5 mm. The effective length and width of the transistor will be different than the drawn length due to the three-dimensional path between source and drain. The device sizes were chosen for convenience of measurement and for proof of concept demonstration. These sizes can easily be scaled down using standard photolithography.

Figure 6:
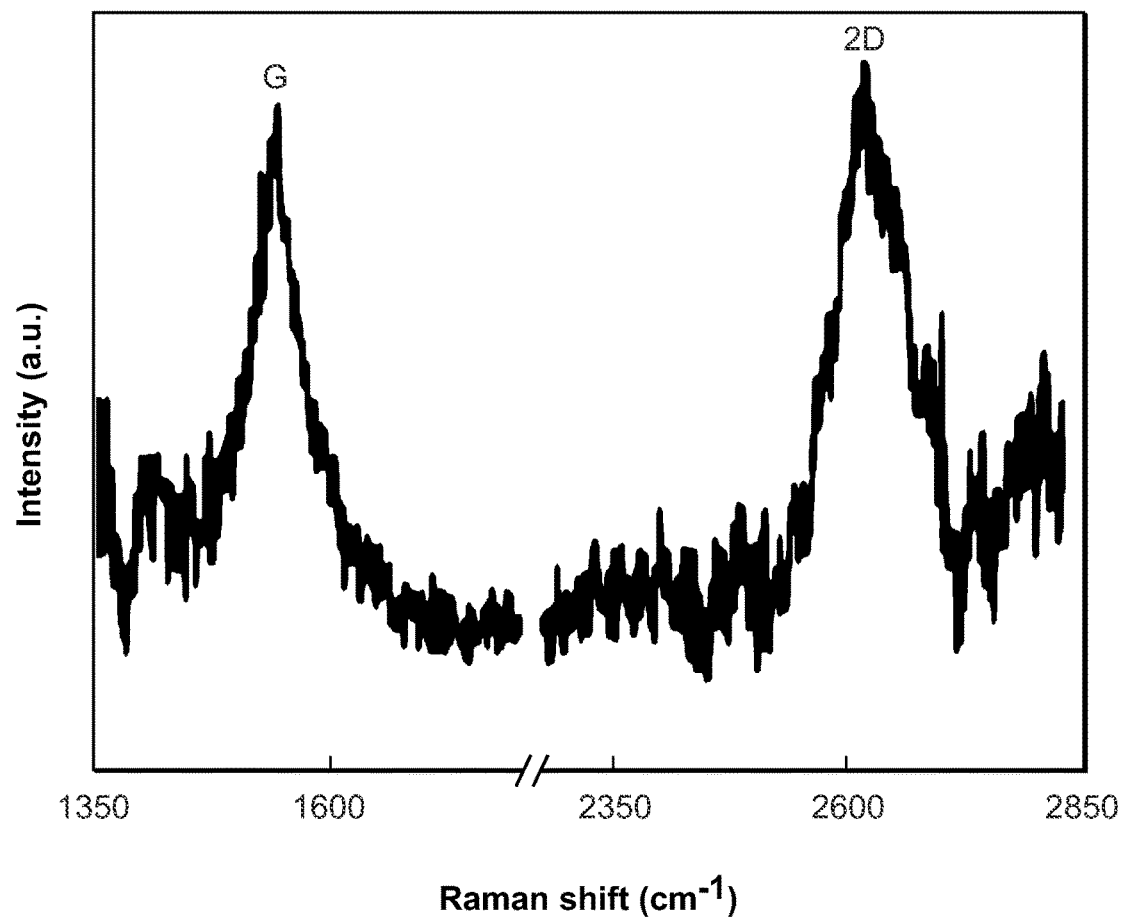
FIG. 6 shows a Raman spectrum of a graphene foam.

FIG. 6 shows the Raman spectrum of the three-dimensional graphene after the copper has been etched away. The Raman shift was studied using a Raman spectrometer (Jasco NRS-3100) with 785 nm laser excitation. Scanning electron microscopy images were taken using Zeiss EVO scanning electron microscopy. Electrical measurements were performed using probe station (Signatone H100) and semiconductor parameter analyzer (HP Agilent 4156A) at room temperature and atmospheric pressure in ambient environment. The C-V measurement was performed using LCR meter (Agilent E4980A, 20 Hz to 2 MHz). As is apparent in FIG. 6, there is a G peak at 1534 cm$^{-1}$ and 2D peak at 2610 cm$^{-1}$ for a 785 nm excitation. The intensity of the G band and 2D band is approximately the same. This implies the existence of bi-layer graphene.

Graphene layers do not have any structural support once the copper has been etched away. As a result, micro and nano-sized shrinks tend to develop. These shrinks degrade the overall mobility of the carriers. Estimated electron and hole mobility of graphene foam after etching away the copper are only 2497 cm$^2$V$^{-1}$s$^{-1}$ and 4023 cm$^2$V$^{-1}$s$^{-1}$ respectively.

The mobility of the carriers can be improved by decreasing the ripples and defects created in graphene and by preventing the collapse and shrinkage in the active layer after etching copper. This can be done by using a supportive layer while etching the copper away and by etching in a more controlled manner, for example by adding etchant at a constant flow rate and by taking steps to reduce overall mechanical vibrations.

While the observed mobility of graphene has been lower than what has been demonstrated for suspended graphene, it is adequate for most analog and sensing applications. Moreover, proposed liquid gated FETs are expected to somewhat inherently slow anyway, simply because of the low mobility of the heavy ions in the ionic liquid. The mobility degradation caused by graphene shrinkage is therefore not a limiting factor and not noticeably affect the overall speed performance of the transistor.

Figure 7:
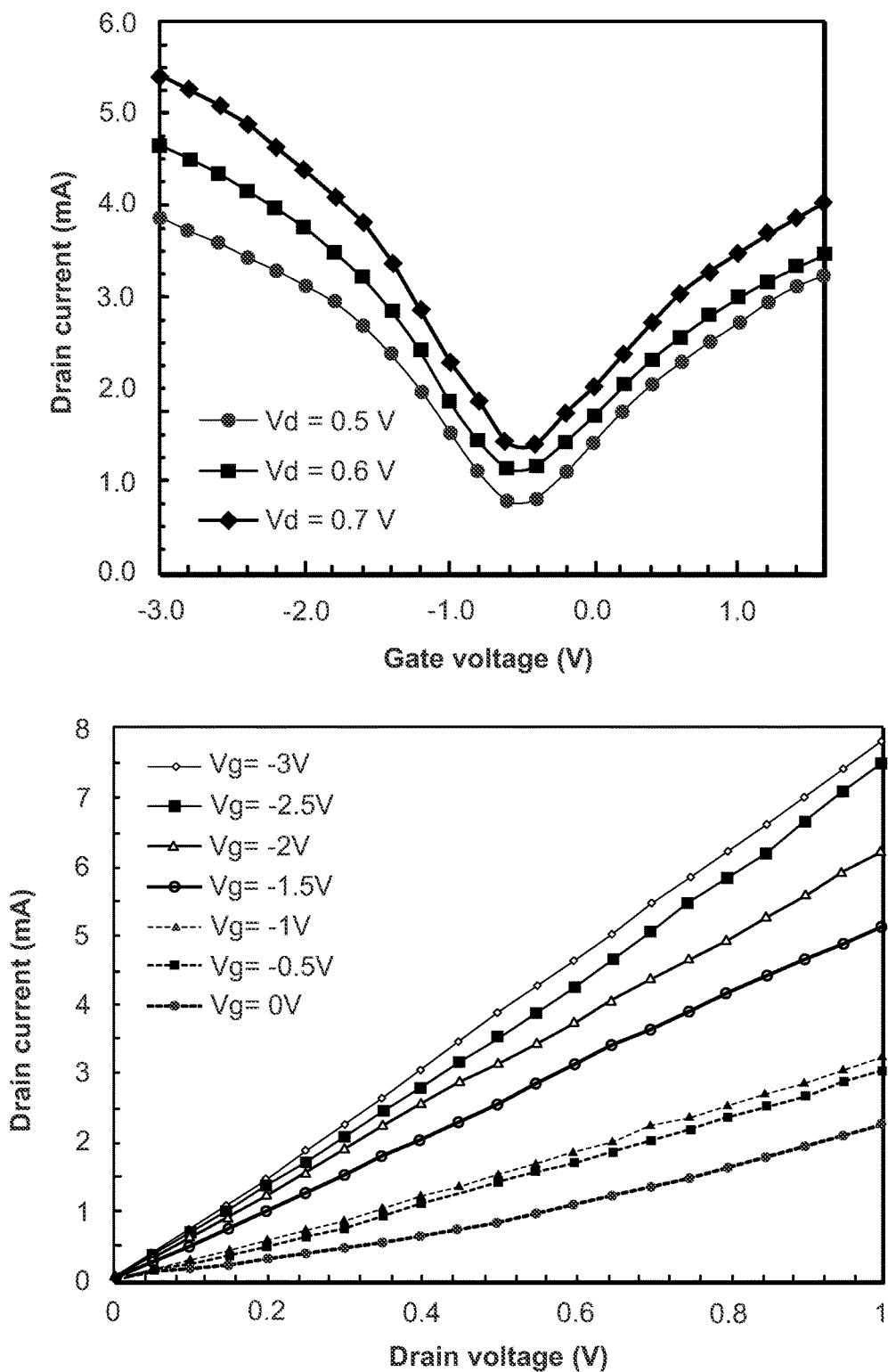
FIG. 7 shows electrical properties of a graphene foam transistor.

FIG. 7 shows the electrical measurement results for a single transistor 22. The left-hand plot shows drain current as a function of gate voltage for three different drain potentials, namely at 0.5, 0.6 and 0.7 V. As is apparent from the slopes, the conductivity of graphene changes sign at around −0.6 volts. This point of minimum conductivity is known as the Dirac point. Its exact value depends on material properties such as doping and impurities.

The behavior shown in the left-hand plot in FIG. 7 is consistent with a zero bandgap material that displays ambipolar electric field effects. Conductivity of the channel decreases as the gate voltage increases from −3 V to −0.6 V. Further increasing the gate voltage from −0.6 V to 1.6 V increases conductivity. Past about 1.6 volts, conductivity saturates.

The type of charge carrier in the channel depends on the gate voltage. A negative gate voltage creates a p-type graphene channel and positive gate voltage creates an n-type channel.

The extracted minimum contact resistance at the source/drain terminal is 6.87 Ωmm and the extracted equivalent sheet resistance of the active layer is 620 Ω/□. Contact resistance and sheet resistance can be improved by decreasing the defects and the ripples in the graphene foam after etching away the copper. The contact resistance decreases as the interface between metal and graphene is improved.

Another way to improve contact resistance is to control base pressure during metal deposition. In the embodiments described herein, the base pressure during the deposition of titanium is $10^{-6}$ Torr. However, further reduction will improve contact resistance. For example, at a base pressure of $8\times10^{-9}$ Torr, contact resistance decreases to less than 250 Ω.μm.

The ionic solution used as a liquid gate is 1-Butyl-3-methylimidazolium hexafluorophosphate (BMM PF$_6$, 98%), which creates a double layer capacitance of approximately 15-nF at the interface with the graphene. This serves as the gate capacitance of the transistor. The on/off current ratio in the device described herein is about 5. In a long channel graphene transistor, the on/off current ratio can be between 2 and 20.

The plot on the right-hand side of FIG. 7 shows the drain current versus drain voltage characteristic of the transistor. As the carrier density increases with increasing drain voltage, the drift velocity does not saturate for small values of V$_{DS}$. Therefore saturation behavior is not observed in graphene transistors.

The electronic performance indicates that liquid gating using high conductivity ionic liquid as a gate provides a high level of electrostatic control over the graphene transistor. This results in high carrier concentration and high mobility in the transistor with very low operating voltages.

A transistor as described herein need not be restricted to a long channel transistor. Such a transistor could be scaled down considerably with standard lithography to achieve even better electronic properties.

A transistor as described herein, with its three dimensional random network, high surface area, and liquid gating is ideally suited as chemical and biological sensor for variety of applications. Due to graphene's highly stable carbonaceous form, it is also biocompatible. The proposed three-dimensional liquid gated transistor is therefore ideal as an electronic interface with a biological system through which it is possible to record electrical signals, to apply electrical stimuli, and to sense chemical and biological parameters in vivo.

The invention claimed is:

1. An apparatus comprising a field-effect transistor having a channel that comprises a three-dimensional graphene foam that comprises an interconnected network of graphene strips, wherein said graphene strips are made of a form of graphene selected from the group consisting of monolayer graphene and bilayer graphene.

2. The apparatus of claim 1, further comprising an ionic liquid, wherein said ionic liquid bathes said foam.

3. The apparatus of claim 2, wherein said ionic liquid comprises 1-Butyl-3-methylimidazolium hexafluorophosphate.

4. The apparatus of claim 1, wherein said strips are made of monolayer graphene.

5. The apparatus of claim 1, further comprising a hydrophilic agent on said graphene.

6. The apparatus of claim 1, wherein said agent comprises $HfO_2$.

7. The apparatus of claim 1, further comprising a sensor, wherein variation in a property of said transistor forms a basis for a measurement by said sensor.

8. The apparatus of claim 7, wherein said sensor comprises a biological sensor.

9. The apparatus of claim 8, wherein said biological sensor is configured for in vivo measurements.

10. The apparatus of claim 7, wherein said sensor comprises a chemical sensor.

11. The apparatus of claim 7, wherein said sensor comprises strain sensor.

12. The apparatus of claim 7, wherein said sensor comprises a pH sensor.

13. The apparatus of claim 1, wherein said transistor incorporates a scaffold.

14. The apparatus of claim 1, wherein said strips are made of bilayer graphene.

15. The apparatus of claim 1, wherein variation in a property of said transistor forms a basis for a measurement of both pH and strain.

16. The apparatus of claim 1, wherein said transistor is a multimodal device that measures multiple inputs at the same time.

17. The apparatus of claim 1, wherein said field-effect transistor comprises a source terminal and a drain terminal, wherein said channel defines a plane having a top side a bottom side, and a perimeter, and wherein said source and drain terminals connect to said perimeter.

18. The apparatus of claim 1, wherein said graphene is suspended above a substrate.

* * * * *